US008716669B2

(12) United States Patent
Miyaoka et al.

(10) Patent No.: US 8,716,669 B2
(45) Date of Patent: May 6, 2014

(54) LINE OF RESPONSE ESTIMATION FOR HIGH-RESOLUTION PET DETECTOR

(75) Inventors: Robert S. Miyaoka, Shoreline, WA (US); Kyle Champley, Ballston Spa, NY (US); Lawrence MacDonald, Seattle, WA (US); Thomas K. Lewellen, Port Ludlow, WA (US)

(73) Assignee: University of Washington, Seattle, WA (US)

( * ) Notice: Subject to any disclaimer, the term of this patent is extended or adjusted under 35 U.S.C. 154(b) by 374 days.

(21) Appl. No.: 13/125,966

(22) PCT Filed: Oct. 22, 2009

(86) PCT No.: PCT/US2009/061600
§ 371 (c)(1),
(2), (4) Date: Oct. 26, 2011

(87) PCT Pub. No.: WO2010/048363
PCT Pub. Date: Apr. 29, 2010

(65) Prior Publication Data
US 2012/0138804 A1 Jun. 7, 2012

Related U.S. Application Data

(60) Provisional application No. 61/108,444, filed on Oct. 24, 2008.

(51) Int. Cl.
*G01T 1/164* (2006.01)
(52) U.S. Cl.
USPC ................. 250/363.03; 250/362; 250/363.01; 250/363.02
(58) Field of Classification Search
USPC .................. 250/362, 363.01, 363.02, 363.03
See application file for complete search history.

(56) References Cited

U.S. PATENT DOCUMENTS 7,129,496 B2 * 10/2006 Stearns et al. ........... 250/363.03
2006/0163485 A1 * 7/2006 Stearns et al. ........... 250/363.03
(Continued)

FOREIGN PATENT DOCUMENTS

| JP | 2005-308738 A | 11/2005 |
| JP | 2008-51701 A | 3/2008 |
| WO | 9708569 A1 | 3/1997 |

OTHER PUBLICATIONS

International Search Report mailed May 18, 2010, issued in corresponding International Application No. PCT/US2009/061600, filed Oct. 22, 2009, 1 page.

(Continued)

*Primary Examiner* — David Porta
*Assistant Examiner* — Djura Malevic
(74) *Attorney, Agent, or Firm* — Christensen O'Connor Johnson Kindness PLLC

(57) ABSTRACT

A method for estimating a line or response in a positron emission tomography scanner having depth of interaction estimation capability. The method utilizes information from both detector modules detecting a coincident event. A joint probability density function combining factors accounting for intermediate Compton scattering interactions and/or a final interaction that may be either a Compton scattering interaction or photoelectric absorption is calculated. In a preferred embodiment, a Bayesian estimation scheme is used to integrate the PDF for all permutations of the measured signal pairs, and the permutation with the largest joint probability is selected to construct the estimated line of response.

18 Claims, 4 Drawing Sheets

(56) References Cited

U.S. PATENT DOCUMENTS

2007/0253530 A1* 11/2007 Mihailescu et al. ............ 378/22
2008/0224050 A1* 9/2008 Thielemans et al. .......... 250/362
2008/0317194 A1* 12/2008 Gagnon et al. .................... 378/4

OTHER PUBLICATIONS

Joung, J., et al., "cMiCE: A High Resolution Animal Pet Using Continuous LSO With a Statistics Based Positioning Scheme," Nuclear Instruments and Methods in Physics Research Section A: Accelerators, Spectrometers, Detectors and Associated Equipment 489(1-3):584-598, Aug. 2002.

Lee, K., et al., "Pragmatic Fully 3D Image Reconstruction for the MiCES Mouse Imaging PET Scanner," Physics in Medicine and Biology 49(19):4563-4578, Oct. 2004.

Ling, T., et al., "Depth of Interaction Decoding of a Continuous Crystal Detector Module," Physics in Medicine and Biology 52(8):2213-2228, Apr. 2007.

Miyaoka, R.S., et al., "Design of a Depth of Interaction (DOI) PET Detector Module," IEEE Nuclear Science Symposium: Conference Record, Albuquerque, N.M., Nov. 9-15, 1997, vol. 2, pp. 939-943.

Nichols, T.E., et al., "Spatiotemporal Reconstruction of List-Mode PET Data," IEEE Transactions on Medical Imaging 21(4):396-404, Apr. 2002.

* cited by examiner

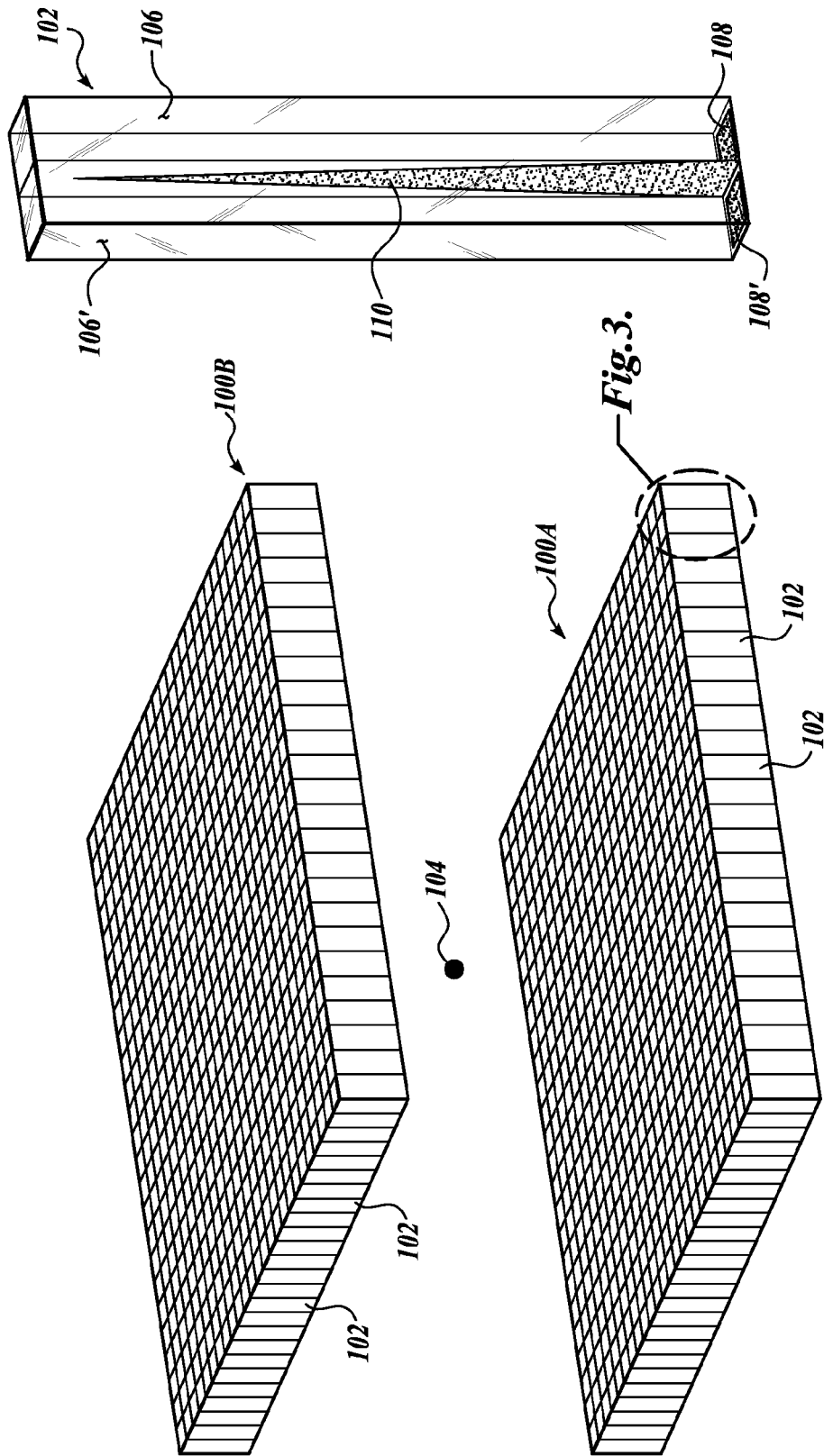

LINE OF RESPONSE ESTIMATION FOR HIGH-RESOLUTION PET DETECTOR

CROSS-REFERENCE TO RELATED APPLICATION

This application claims the benefit of U.S. Provisional Application No. 61/108,444, filed Oct. 24, 2008, the disclosure of which is hereby expressly incorporated by reference in its entirety.

STATEMENT OF GOVERNMENT LICENSE RIGHTS

This invention was made with Government support under Contract No. EB002117 awarded by (NIBIB) National Institute of Biomedical Imaging and BioEngineering. The Government has certain rights in the invention.

BACKGROUND

The ability to produce images of the inside of a living organism without invasive surgery has been a major advancement in medicine over the last one hundred years. Imaging techniques such as X-ray computer tomography (CT) and magnetic resonance imaging (MRI) have given doctors and scientists the ability to view high-resolution images of anatomical structures inside the body. While this has led to advancements in disease diagnosis and treatment, a large set of diseases causes changes in anatomical structure only in the late stages of the disease or never at all. This has given rise to a branch of medical imaging that captures certain metabolic activities inside a living body. Positron emission tomography (PET) is in this class of medical imaging.

Positron Emission Tomography

PET is a medical imaging modality that takes advantage of radioactive decay to measure certain metabolic activities inside living organisms. PET imaging systems comprise three main components, indicated schematically in FIG. 1, a radioactive tracer that is administered to the subject to be scanned, a scanner that is operable to detect the location of radioactive tracer (indirectly as discussed below), and a tomographic imaging processing system.

The first step is to produce and administer a radioactive tracer 90, comprising a radioactive isotope and a metabolically active molecule. The tracer 90 is injected into the body to be scanned 91. After allowing time for the tracer 90 to concentrate in certain tissues, the body 91 is positioned inside the scanner 92. The radioactive decay event for tracers used in conventional PET studies is positron emission. Radioactive decay in the tracer 90 emits a positron $e^+$. The positron $e^+$ interacts with an electron $e^-$ in the body in an annihilation event that produces two 511 KeV anti-parallel photons or gamma photons γ. The scanner 92 detects at least some of the 511 KeV photons γ generated in the annihilation event.

The scanner 92 includes a ring of sensors and front-end electronics that process the signals generated by the sensors. The sensors typically comprise scintillator crystals or scintillators 93 and photomultiplier tubes (PMT), silicon photomultipliers (SiMP) or avalanche photo diodes (APD) 94. The scintillator 93 interacts with the 511 KeV gamma photons γ to produce many lower-energy photons, typically visible light photons. The PMT, SiMP, or APD 94 detects the visible light photons and generate a corresponding electrical pulse or signal. The electric pulses are processed by front-end electronics to determine the parameters or characteristics of the pulse (i.e., energy, timing). Unless the context implies otherwise, for convenience references to a PMT, SiMP or APD herein will be understood to include any mechanism or device for detecting gamma photons such as 511 KeV photons and producing lower-energy photons such as visible light photons in response.

Finally, the data is sent to a host computer 95 that performs tomographic image reconstruction to turn the data into a 3-D image.

Radiopharmaceutical

To synthesize the tracer 90, a short-lived radioactive isotope is attached to a metabolically active molecule. The short half-life reduces the subject's exposure to ionizing radiation, but generally requires the tracer 90 be produced close to the scanner. The most commonly used tracer is fluorine-18 flourodeoxyglucose ([F-18]FDG), an analog of glucose that has a half-life of 110 minutes. [F-18]FDG is similar enough to glucose that it is phosphorylated by cells that utilize glucose, but does not undergo glycolysis. Thus, the radioactive portion of the molecule becomes trapped in the tissue. Cells that consume a lot of glucose, such as cancers and brain cells, accumulate more [F-18]FDG over time relative to other tissues.

After sufficient time has passed for the tissue of interest to uptake enough tracer 90, the scanner 92 is used to detect the radioactive decay events, i.e., by detecting the 511 KeV photons. When a positron is emitted, it typically travels a few millimeters in tissue before it annihilates with an electron, producing two 511 KeV photons directed at 180°±23° from one another.

Photon Scintillation

Most of the 511 KeV photons will pass through the body tissue (and other materials) without significant interaction. While this typically allows the photon to travel through and exit the body, the gamma photons are difficult to detect. Photon detection is the task of the scintillator 93. A scintillator 93 absorbs gamma photons and emits lower energy photons, typically visible light photons. A scintillator 93 can be made from various materials including plastics, organic and inorganic crystals, and organic liquids. Each type of scintillator has a different density, index of refraction, timing characteristics, and wavelength of maximum emission.

In general, the density of the scintillator crystal determines how well the material stops the gamma photons. The index of refraction of the scintillator crystal and the wavelength of the emitted light affect how easily light can be collected from the crystal. The wavelength of the emitted light also needs to be matched with the device that will turn the light into an electrical pulse (e.g., the PMT) in order to optimize the efficiency. The scintillator timing characteristics determine how long it takes the visible light to reach its maximum output (rise time) and how long it takes to decay (decay time). The rise and decay times are important because the longer the sum of these two times, the lower the number of events a detector can handle in a given period, and thus the longer the scan will take to get the same number of counts. Also, the longer the timing characteristics, the greater the likelihood that two events will overlap (pile-up) and data will be lost.

The 511 KeV photons may undergo two types of interactions within the scintillator 93—Compton scattering, wherein the photon will lose energy and change direction, and photoelectric absorption. For example, a particular gamma photon may (i) experience photoelectric absorption in its first interaction in the scintillator crystal, (ii) undergo Compton scattering one or more times within the crystal prior to photoelectric absorption, or (iii) may undergo Compton scattering one or more times within the crystal before being ejected from the crystal.

Photomultiplier Tubes

Attached to the scintillator 93 are electronic devices that convert the visible light photons from the scintillator 93 into electronic pulses. The two most commonly used devices are PMTs and APDs. A PMT is a vacuum tube with a photocathode, several dynodes, and an anode that has high gains to allow very low levels of light to be detected. An APD is a semiconductor version of the PMT. Another technology that is currently being studied for use in PET scanners is SiPM. SiPMs comprise an array of semiconducting photodiodes that operate in Geiger mode so that when a photon interacts and generates a carrier, a short pulse of current is generated. In an exemplary SiPM, the array of photodiodes comprises about 103 diodes per $mm^2$. All of the diodes are connected to a common silicon substrate so the output of the array is a sum of the output of all of the diodes. The output can therefore range from a minimum wherein one photodiode fires to a maximum wherein all of the photodiodes fire. This gives these devices a linear output even though they are made up of digital devices.

Image Reconstruction

An important advantage of PET imaging is that the annihilation event produces two substantially anti-parallel 511 KeV photons. Therefore, with detectors disposed around the body being imaged, two detection interactions may be observed at roughly the same time (coincident interactions) in two oppositely-disposed detector modules. (Throughout this document, detector modules, sensors, etc. that are disposed opposite each other means refers to distinct detector modules that are within each others field of view.) The annihilation event producing the 511 KeV photons will be located somewhere on the line connecting the two photon detection points. The line connecting two coincident interactions is referred to as the line of response (LOR). When enough coincident events have been detected, image reconstruction can begin. Essentially the detected events are separated into parallel lines of response (interpreted path of photon pair) that can be used to create a 3-D image using computer tomography. Methods for creating images using computer tomography are well known in the art. It will be appreciated that the accuracy of the 3-D PET images is dependent on the accuracy of the estimated LORs.

While PET, MRI, and CT are all common medical imaging techniques, the information obtained from the different modalities is quite different. MRI and CT give anatomical or structural information. That is, they produce a picture of the inside of the body. This is great for problems such as broken bones, torn ligaments or anything else that presents as abnormal structure. However, MRI and CT do not indicate metabolic activity. This is the domain of PET. The use of metabolically active tracers means that the images produced by PET provide functional or biochemical information.

Oncology (study of cancer) is currently the most common application of PET. Certain cancerous tissues metabolize more glucose than normal tissue. [F-18]FDG is close enough to glucose that cancerous cells readily absorb it and, therefore, they have high radioactive activity relative to background tissue during a scan. This enables a PET scan to detect some cancers before they are large enough to be seen on an MRI scan. PET scan information is also very useful for monitoring treatment progression as the quantity of tracer uptake can be tracked over the progression of the therapy. If a scan indicates lower activity in the same cancerous tissue after therapy, it indicates the therapy is working.

PET is also useful in neurology (study of the nervous system) and cardiology (study of the heart). An interesting application in neurology is the early diagnosis of Parkinson's disease. Tracers have been developed that concentrate in the cells in the brain that produce dopamine, a neurotransmitter. In patients with Parkinson's disease, neurons that produce dopamine reduce in number. Therefore, a scan of a Parkinson's patient would have less activity than a healthy patient's. This can lead to early diagnosis, since many of the other early signs of Parkinson's are similar to other diseases.

There remains a need for continued improvements in the cost, efficiency and accuracy of PET systems.

SUMMARY

This summary is provided to introduce a selection of concepts in a simplified form that are further described below in the Detailed Description. This summary is not intended to identify key features of the claimed subject matter nor is it intended to be used as an aid in determining the scope of the claimed subject matter.

A statistical method is disclosed for estimating the line of response corresponding to an annihilation event detected in a PET scanner. In an exemplary embodiment of the method, a coincident event is identified when a first detector module and a suitable second detector module both detect one or more photon producing interaction that occur close enough in time to be considered coincident for purposes of positron emission tomography. The method then selects one of the photon-producing interactions in each of the detector modules and calculates a joint probability that the selected interactions are the first-occurring interactions in both modules. This step is repeated for all permutation of combinations of one photon-producing event from each of the detector modules. The permutation that produces the largest joint probability is then used to construct a line of response.

In an embodiment of the invention the joint probability calculation is performed using a joint probability density function that includes factors accounting for Compton scattering interactions in the detector modules and factors accounting for a final interaction in each module, wherein the final interaction may be either Compton scattering or photoelectric absorption.

In an embodiment of the invention the first and second detector modules have detector elements that produce signals that depend on the depth of interaction within the detector element, such that the detected signals provide information that can be used to estimate the axial position of the interaction within the detector element.

In an embodiment of the invention a Bayesian estimation is used for calculating the joint probability that the selected photon-producing interactions are the first occurring photon-producing interactions in both of the first and second detector modules for the identified coincident event.

In an embodiment of the invention identified event is discarded if the largest calculated joint probability is less than a selected threshold.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 shows schematically a pair of oppositely disposed detector modules;

FIG. 3 shows an exemplary prior art dMiCE crystal pair detector element, suitable for use in the detector modules shown in FIG. 2;

DETAILED DESCRIPTION

Figure 1:
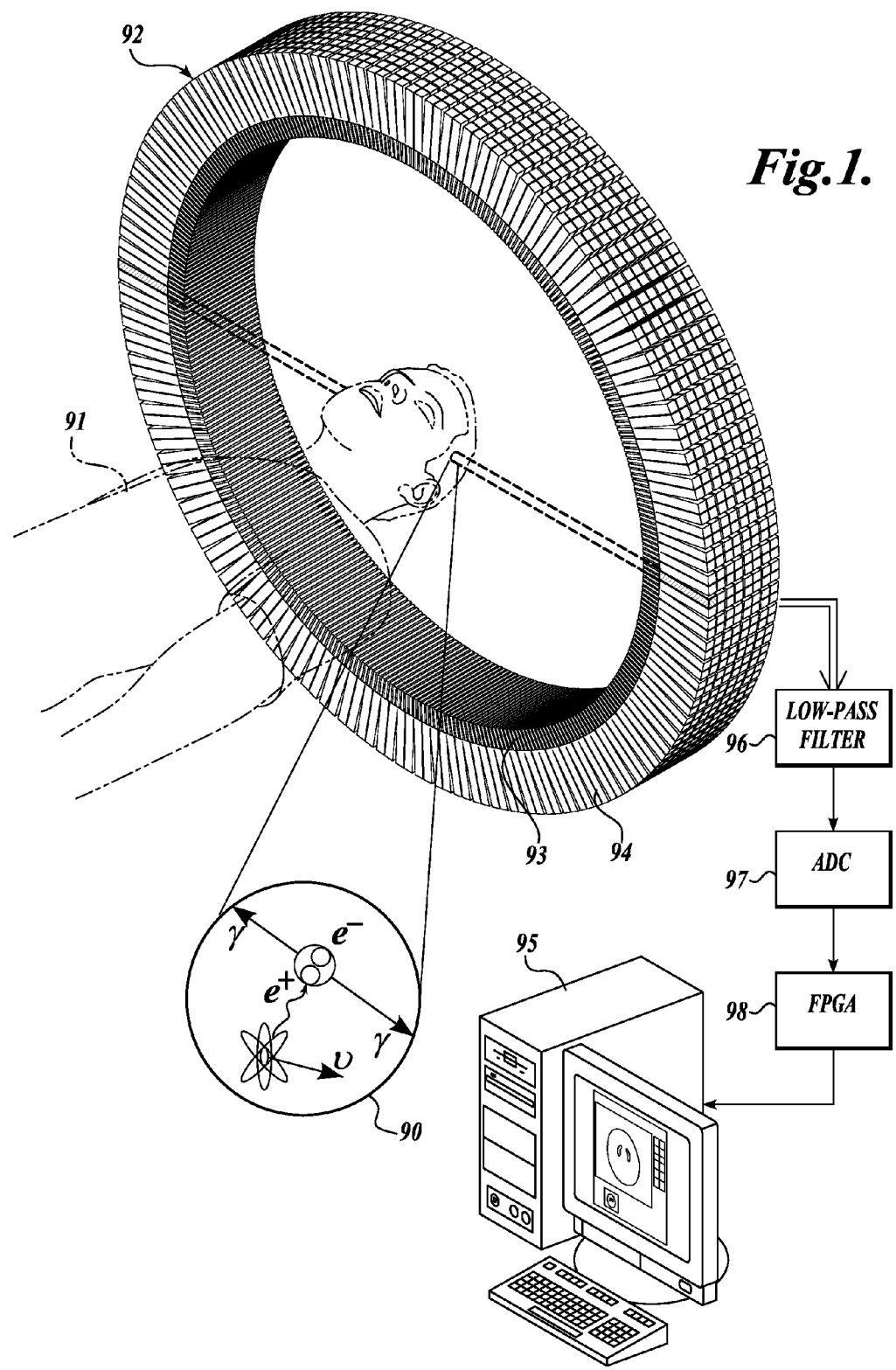
FIG. 1 is an environmental view showing a PET scanner system in accordance with the present invention.

A description of particular embodiments of a PET system in accordance with the present invention will now be described with reference to the figures, wherein like numbers indicate like parts. Referring again to FIG. 1, a high-resolution PET scanner 92 is shown schematically with detectors comprising scintillators 93 and PMTs 94. Sensor data is filtered with a low-pass filter 96, digitized with an analog to digital converter 97, and the digitized data is initially processed with field programmable gate arrays (FPGAs) 98. An exemplary method and apparatus for data acquisition in PET systems is disclosed in co-pending U.S. patent application Ser. No. 12/264,093, published on Sep. 10, 2009 in U.S. Patent Application Publication No. 2009/0224158, which is hereby incorporated by reference in its entirety.

FIG. 2 illustrates schematically two opposed detector modules 100A and 100B, each module comprising an array of detector elements 102. For example, a suitable dMiCE crystal pair detector element 102 is shown in FIG. 3. The detector modules 100A and 100B may represent any two detector modules that are within the relevant field of view in a PET scanner. A source of gamma photons 104 between the two detector modules 100A, 100B, for example annihilation events as discussed above, may produce a coincident detection event in the modules. In the present application "coincident" detection interactions are interactions in two modules that occur close enough in time to be considered coincident for purposes of PET, and are assumed to result from a single annihilation event. For example, detection interactions in two detector modules 100A, 100B that are within a relevant field of view may be considered coincident if they occur within a ten nanosecond period. The actual time span threshold will depend on the particular apparatus and application. Several factors may contribute to the gamma photons in an annihilation event having slightly differing detection times, including the particular location of the annihilation event within the scanner, finite timing resolution of the detector, etc.

The exemplary dMiCE crystal pair detector element 102, illustrated in FIG. 3, comprises a pair of crystals 106, 106', each crystal having a photodetector such as a micro-pixel APD 108, 108' at a distal end. A triangular reflector 110 is disposed between the two crystals 106, 106', such that the signals from the APDs 108, 108' resulting from gamma photon interactions within the crystal pair will depend on the location of the interaction within the crystal pair.

As discussed above, the line of response (LOR) connecting coincident detection interactions in two spaced detectors is used in computer tomography to generate the medical images from PET scans. Accuracy in identifying the LOR is therefore important to the accuracy of the generated images. Two sources of error in identifying the LOR are illustrated in FIGS. 4A and 4B.

Figure 4A:
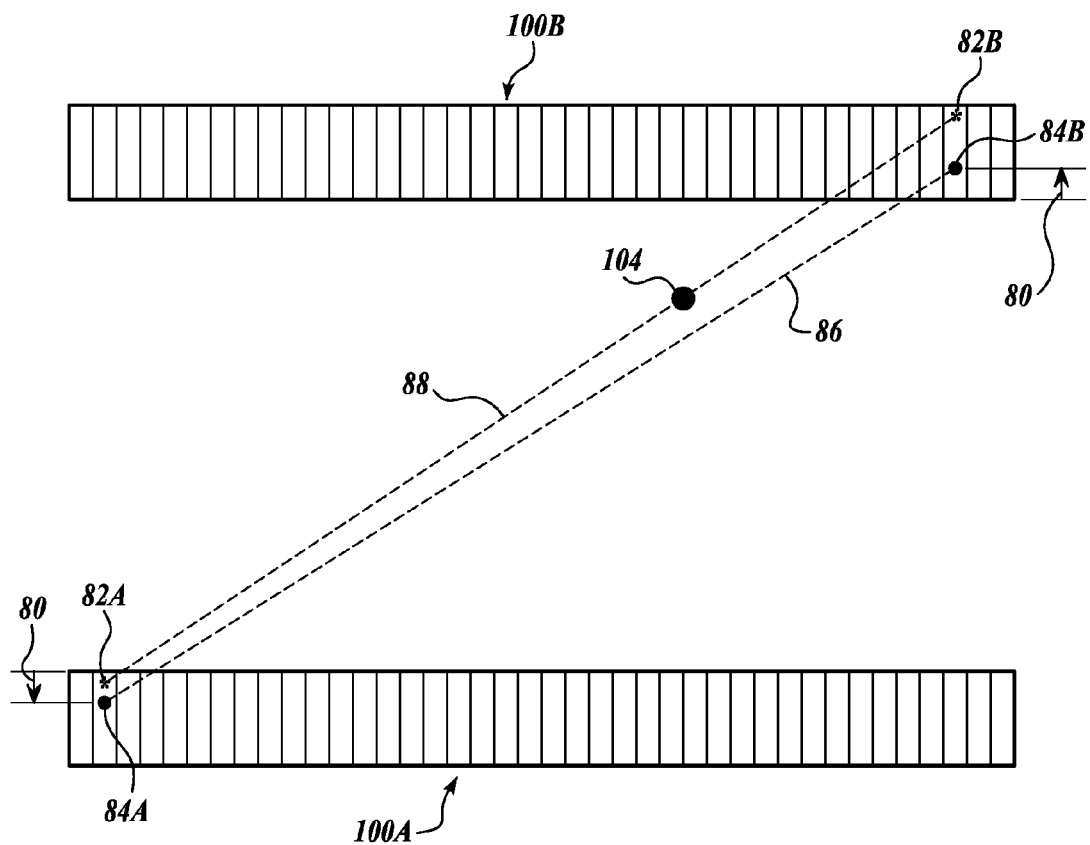
FIGS. 4A and 4B show schematically sources of error in estimating line of response information in a conventional PET detector, FIG. 4A showing parallax error resulting from lack of depth of interaction information and FIG. 4B showing error resulting from multiple interactions.

FIG. 4A illustrates the well-known parallax error. Conventional commercial PET scanners do not measure the axial location of an interaction within the crystal (the depth of interaction, or DOI), but rather assign a constant value 80 to the DOI for all detected interactions, based on the attenuation coefficient of the detector crystal 100A, 100B. In FIG. 4A exemplary interaction locations 82A, 82B are shown. Interaction locations 84A, 84B based on an assumed constant DOI 80 are also shown. An estimated LOR 86 is used comprising a line connecting the fixed-DOI interaction locations 84A, 84B. The estimated LOR 86 is significantly different from the "true" LOR 88, i.e., the line connecting the interaction locations 82A, 82B.

Parallax error may be reduced by using detector elements 102 that are sensitive to the DOI of the detection interaction within the crystal, such as the dMiCE detector element 102 discussed above, and described in more detail in "New Directions for dMiCE-a Depth-of-Interaction Detector Design for PET Scanners," T. K. Lewellen et al., *IEEE Nucl. Sci. Symp. Conf. Rec.* (1997), 2007; 5:3798-3802, which is hereby incorporated by reference in its entirety. It remains desirable to improve the accuracy of the DOI estimation.

Figure 4B:
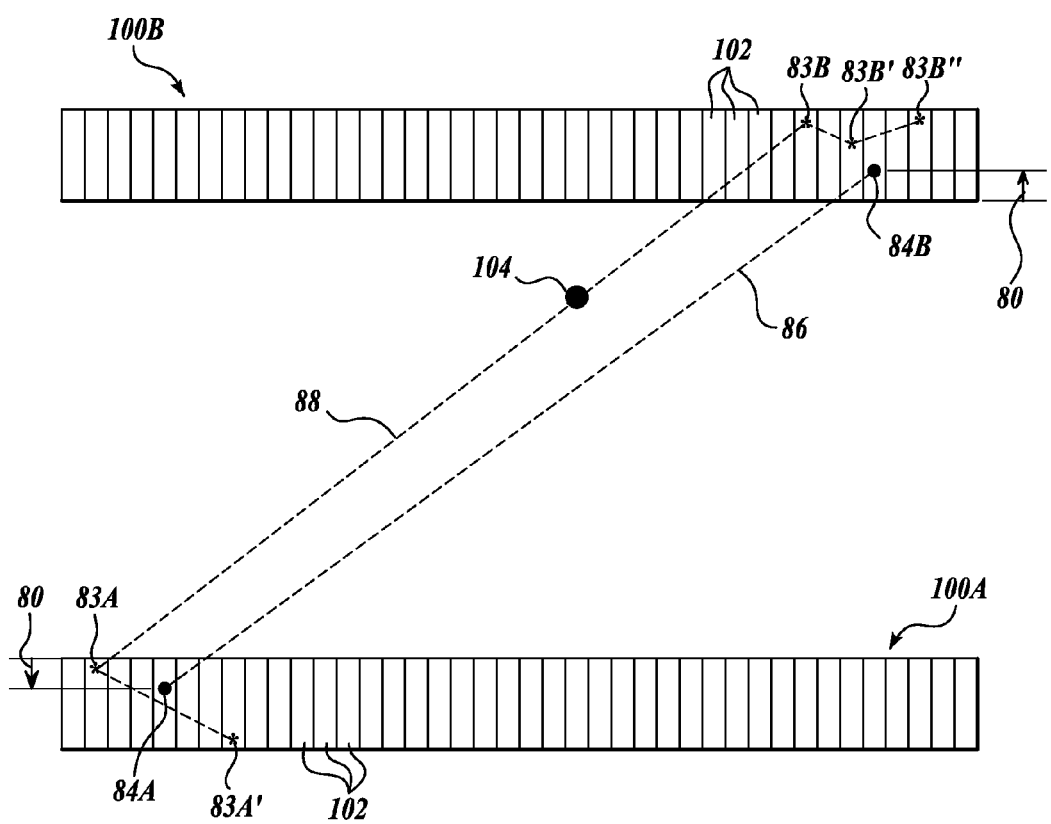

FIG. 4B schematically illustrates a second source of error in estimating the LOR resulting from a coincident photon undergoing multiple interactions within a detector module. A gamma photon may undergo two types of photon-producing interactions within a scintillation crystal: Compton scattering wherein a portion of the photon is surrendered and the photon direction of travel is changed; and photoelectric absorption wherein all of the photon energy is surrendered. More than one Compton scattering interaction may occur before the gamma photon is either absorbed or escapes the crystal.

As illustrated in FIG. 4B the gamma photon entering the first detector module 100A undergoes a first interaction 83A (Compton scattering) and a second interaction 83A'. The gamma photon entering second detector module 100B undergoes a first interaction 83B, a second interaction 83B' and a third interaction 83B". Each of these interactions produce photons detected by the associated detector element 102.

When multiple photon-producing interactions occur, typical prior art methods will either use estimated interaction location 84A and 84B, for example using the assumed DOI 80 and a weighted average of the multiple interactions locations for each detector module 100A, 100B, or will simply disregard the event. The estimated interaction locations 84A, 84B are then used to generate the estimated LOR 86, which may vary significantly from the "true" LOR 88.

In a typical detector, fewer than half of the gamma photons entering a scintillation crystal will undergo photoelectric absorption as the first (and only) photon-producing interaction within the crystal. Therefore, on average fewer than 25% of the coincident pairs will result from an annihilation event wherein both gamma photons interacted only once within a detector module.

If the first interaction within the detector module could be determined, the estimation of the true LOR 88 could be greatly improved. However, the multiple interactions within the detector module occur very close in time and at varying distances from the photodetectors. It is not currently practical to determine the time sequence of multiple interactions based on the time of detection of the multiple interactions.

A method is disclosed herein for improving the estimation of the LOR in PET scanners. In the present method the light responses (detector module signals) resulting from the two anti-parallel annihilation gamma photons are jointly analyzed to identify the most likely first interaction within each detector module to estimate the LOR. In the preferred embodiment, the statistical analysis also provides an estimate of the DOI of the identified first interaction.

An additional aspect of the currently preferred method is that a likelihood or probability that the estimated LOR accurately selects the correct first interaction within each of the detector modules is calculated. It is contemplated that the estimation of the probability that the identified first interactions are correctly identified may be used to filter out anomalous coincident events. For example, if the method determines the probability the identified first interactions are correctly identified is less than an experimentally-determined threshold value the detection event may be ignored.

Although the currently preferred embodiment will be disclosed with reference to the dMiCE crystal pair detector elements 102 shown in FIG. 3, the method may be readily modified by persons of skill in the art to other detector element configurations. For example, detector elements are know wherein photodetector elements are provided on both ends of the crystal detector elements which provides information that may be used to estimate the DOI.

To verify the current method detector modules 110A, 100B with dMiCE-type crystal pair detector elements 102 were simulated with individual crystals having a size of 200×200× 20 mm$^3$, and the modules 100A and 100B are separated by 100 mm. Using a pair of large panel detectors in close proximity allows testing the effect of estimating LORs with a large oblique angle.

Let $M=(M_a,M_b)^T$ represent the signals measured by the micro-pixel APDs 108, 108' in a crystal pair detector element 102, wherein $M_a$ is the primary detector pixel, i.e., for the individual crystal in which the interaction occurred, and $M_b$ is the secondary detector pixel. We model the distribution of measured signals M|x, λ (where λ is the energy deposited) as a joint Gaussian whose mean and variance are described as follows. The mean light response is modeled to vary linearly with depth:

$$E[M_p|z,\lambda]=(r_p z+b_p)\lambda$$

$$Var[M_p|z,\lambda]=(dE[M_p|z,\lambda])^2$$

$$E[M_s|z,\lambda]=(r_s z+b_s)\lambda$$

$$Var[M_s|z,\lambda]=(dE[M_s|z,\lambda])^2 \qquad (0)$$

where $r_p$, $r_s$ and $b_p$, $b_s$ are the slope and intercept parameterization for the primary (p) and secondary (s) crystals, d is the energy resolution and z is the depth of the interaction.

A point source is positioned halfway between the two detector modules 100A, 100B and one hundred thousand coincidences with an isotropic distribution (limited to 60° acceptance angle) were simulated. Photon interactions within the detector modules were simulated with a Monte Carlo-based simulation. The output of this software was fed through a program that simulated the noisy detector signals. All coincidences were processed by our estimation algorithms, i.e., no LORs were filtered out due to the total amount of energy deposited in the detector module.

As discussed in detail below, a Bayesian LOR estimation algorithm estimates the positions of the first points of interaction of a photon coincidence pair by calculation of equation (6) and the signal pair order is estimated by equation (5). All integrals are computed using the trapezoid rule.

Performance of the various estimators was measured based on its ability to correctly position the first point of interaction and its overall effect at estimating an LOR.

The bias and variance of the estimated depth of interaction was measured by the sample mean and variance of the difference of the true and estimated depth of the first interaction. In the case of multiple interactions, the Bayesian LOR estimator not only estimates the depth of interaction, but also which interaction was first. We define the misorder rate to be the percentage of events in which the estimator incorrectly determined which interaction was first. Thus if $\hat{i}$ (a permutation) is the estimated ordering of the detector signal pairs and i is the correct ordering of the signal pairs, then the misorder rate is defined as $P(\hat{i}_1 \neq i_1|N \geq 2)$, where N is a random variable for the number of interactions within a detector module. The overall estimation error was measured by the sample mean of the difference between the true and estimated positions of the first interaction.

To illustrate the performance of each estimator in accurately estimating an LOR, we employed focal plane tomography. In focal plane tomography, the estimated LORs are backprojected onto the plane containing the point source and parallel to the face of the detector modules.

Statistical LOR Estimation

In this section we develop a Bayesian LOR estimation algorithm. All probability density functions (PDFs) will be denoted by $f(\cdot)$. We start by developing a probabilistic model of the photon process.

The Photon Process

The process of photon interactions in matter is a well-developed stochastic process. For purposes of speed of computation, we use a simplified model of this process. Our model considers the energy-dependent distribution of photoelectric absorption and Compton scatter. Angular distributions of photons that undergo Compton scatter are modeled by the well-known Klein-Nishina formula. We do not consider positron range, noncolinearity of positron annihilation, photon polarization, or coherent (Rayleigh) scatter. Random variables will be denoted by capital letters and realizations of random variables will be denoted by lower case letters.

Let $X_k$ denote the three-dimensional interaction positions of an annihilation photon. For a coincidence pair we will add a subscript to $X_k$ (e.g., $X_{Ak}$, $X_{Bk}$) to denote the detector module where the annihilation photon interacts. Thus $X_{A2}$ denotes the position of the second interaction of the annihilation photon in detector module A. Let $\Gamma_k$ denote the energy (keV) of the photon after the k-th interaction and $\Lambda_k=\Gamma_{k-1}-\Gamma_k$ denote the energy (keV) deposited by the k-th interaction. The trajectory of the photon after the k-th interaction will be denoted by $$R_k = \frac{X_{k+1} - X_k}{\|X_{k+1} - X_k\|}.$$

The triplets $(X_0,\Gamma_0,R_0)$ are a special case and represent the position, energy, and trajectory of the photon as it first enters the detector module.

Let $\mu_\tau(\gamma)$ be the photo-electric absorption coefficient and $\mu_o(\gamma)$ be the Compton scatter attenuation coefficient of the scintillation material. The total attenuation coefficient is given by $\mu(\gamma)=\mu_\tau(\gamma)+\mu_o(\gamma)$. From the Klein-Nashina formula the probability that a photon of energy $\gamma_{k-1}$ will have energy $\gamma_k$ after undergoing Compton scatter is given by $$f(\gamma_k \mid \gamma_{k-1}) = \frac{1 + \left(\frac{\gamma_k}{\gamma_{k-1}}\right)^2 + \left(\frac{\gamma_k}{\gamma_{k-1}}\right)\left[\left(\frac{511}{\gamma_{k-1}} - \frac{511}{\gamma_k} + 1\right)^2 - 1\right]}{\gamma_k \gamma_{k-1}} \times$$

$$C(\gamma_{k-1}) \begin{cases} 1, & \frac{511\gamma_{k-1}}{511+2\gamma_{k-1}} \leq \gamma_k \leq \gamma_{k-1} \\ 0, & \text{otherwise} \end{cases}$$

The angle of scatter is then given by:

$$\theta(\gamma_k, \gamma_{k-1}) = \cos^{-1}\left(\frac{511}{\gamma_{k-1}} - \frac{511}{\gamma_k} + 1\right).$$

The term $C(\gamma_{k-1})$ is a normalizing factor such that:
$\int_R f(\gamma_k|\gamma_{k-1})d\gamma_k = 1$.

Note that:
$\langle r_k, r_{k-1} \rangle = \cos\theta(\gamma_k,\gamma_{k-1})$.

The probability density function of the photon process of a coincidence pair with k total interactions in detector A and l total interactions in detector B is given by $$f(\gamma_{Ak}, x_{Ak}, \ldots, x_{A1}, \gamma_{Bl}, x_{Bl}, \ldots, x_{B1}) = \quad (1)$$
$$[\delta(\gamma_{A,k})\mu_\tau(\gamma_{A,k-1}) + f(\gamma_{A,k}|\gamma_{A,k-1})\mu_\sigma(\gamma_{A,k-1})]$$
$$e^{-\mu(\gamma_{A,k-1})\|x_{A,k-1}-x_{A,k}\|} \times$$

$$\frac{1}{(2\pi)^{k-1}}\prod_{i=1}^{k-1} f(\gamma_{A,i}|\gamma_{A,i-1})\mu_\sigma(\gamma_{A,i-1})e^{-\mu(\gamma_{A,i-1})\|x_{A,i-1}-x_{A,i}\|} \times \quad (2)$$

$$[\delta(\gamma_{B,l})\mu_\tau(\gamma_{B,l-1}) + f(\gamma_{B,l}|\gamma_{B,l-1})\mu_\sigma(\gamma_{B,l-1})]e^{-\mu(\gamma_{B,l-1})\|x_{B,l-1}-x_{B,l}\|} \times \quad (3)$$

$$\frac{1}{(2\pi)^{l-1}}\prod_{j=1}^{l-1} f(\gamma_{B,j}|\gamma_{B,j-1})\mu_\sigma(\gamma_{B,j-1})e^{-\mu(\gamma_{B,j-1})\|x_{B,j-1}-x_{B,j}\|} \quad (4)$$

where $\delta(\bullet)$ is the Dirac delta function.
Note that:

$$\gamma_{A,i} = \frac{511}{\frac{511}{\gamma_{A,i-1}} + 1 - \langle r_{A,i-1}, r_{A,i}\rangle}$$

for $i=1, 2, \ldots, k-1$ and $$r_{A,0} = \frac{x_{A,1} - x_{B,1}}{\|x_{A,1} - x_{B,1}\|}.$$

Similar equations exist for $\gamma_{B,j}$ and $r_{B,0}$. The entrance positions, $x_{A,0}$ and $x_{B,0}$ can be calculated from $x_{A,1}$ and $x_{B,1}$ and knowledge of the geometry of the scanner. We will assume that $\gamma_{A,0}=\gamma_{B,0}511$ keV.

Equations (2) and (4) account for the first k−1 and l−1 Compton scattering interactions. Equations (1) and (3) account for the final interaction, which could be a photoelectric or Compton scattering interaction wherein the photon escapes the detector. The exponential terms characterize the probability that a photon will travel a certain distance before going through a photo-electric absorption or Compton scattering interaction. If both photons of the coincidence pair interact exactly once, the above distribution reduces to:

$$f(\gamma_{A,1},x_{A,1},\gamma_{B,1},x_{B,1}) = [\delta(\gamma_{A,1})\mu_\tau(\gamma_{A,0}) + f(\gamma_{A,1}|\gamma_{A,0})\mu_\sigma(\gamma_{A,0})]e^{-\mu(\gamma_{A,0})\|x_{A,0}-x_{A,1}\|} \times [\delta(\gamma_{B,1})\mu_\tau(\gamma_{B,0}) + f(\gamma_{B,1}|\gamma_{B,0})\mu_\sigma(\gamma_{B,0})]e^{-\mu(\gamma_{B,0})\|x_{B,0}-x_{B,1}\|}$$

Our Bayesian LOR estimation algorithm estimates the first point of interaction of each photon in a coincidence pair. We assume that each signal pair M was produced by exactly one interaction of a high-energy photon. With this assumption, the order of the interactions is equivalent to the order of the signal pairs produced.

The signal pairs generated by the sequences of high energy photon interactions of a coincidence pair will be denoted by $m_{A,1}, \ldots, m_{A,k}$ and $m_{B,1}, \ldots, m_{B,l}$. The numerical subscripts are arbitrary and do not imply the order of the signals. We must estimate the order of the signal pairs, since this information is unknown. Let $i=(i_1, i_2, \ldots, i_k)$ be a permutation of $(1, 2, \ldots, k)$ and $j=(j_1, j_2, \ldots, j_l)$ be a permutation of $(1, 2, \ldots, l)$. The order of interaction is estimated by:

$$(\hat{i}_1, \ldots, \hat{i}_k, \hat{j}_1, \ldots, \hat{j}_l) \equiv \quad (5)$$
$$\underset{i,j}{\operatorname{argmax}} f(m_{A,i_1}, \ldots, m_{A,i_k}, m_{B,j_1}, \ldots, m_{B,j_l}),$$

where the max is taken over all permutations of the signal pairs. The estimates of the first signal pairs for each of the coincidence photons are $m_{\hat{i}_1}$ and $m_{\hat{j}_1}$. Note that:

$$f(m_{A,2}, m_{A,3}, m_{A,1}, m_{B,1}, m_{B,2})$$

is the probability that $m_{A,2}$, $m_{A,3}$, and $m_{A,1}$ are the first, second, and third signal pairs produced in detector A and $m_{B,1}$, $m_{B,2}$ are the first and second signal pairs produced in detector B. Thus equation (5) is a type of maximum likelihood (ML) estimation because the order of the signals is implicitly assumed (i.e., in the above we implicitly conditioned on the order of the signals).

Consider an arbitrary ordering of the signal pairs. For convenience, we let:

$$\underline{x}_A \equiv (x_{A,k}, \ldots, x_{A,1}), \underline{x}_B \equiv (x_{B,l}, \ldots, x_{B,1})$$

$$\underline{m}_A \equiv (m_{A,k}, \ldots, m_{A,1}), \underline{m}_B \equiv (m_{B,l}, \ldots, m_{B,1})$$

We estimate the points of first interaction of a coincidence pair by Bayesian estimation, which is given by:

$$\begin{bmatrix}\hat{x}_{A1}\\\hat{x}_{B1}\end{bmatrix} \equiv E[(X_{A1}, X_{B1})^T | \underline{m}_A, \underline{m}_B] \quad (6)$$

$$= \frac{\int\cdots\int \begin{bmatrix}x_{A1}\\x_{B1}\end{bmatrix} f(\underline{x}_A, \underline{x}_B | \underline{m}_A, \underline{m}_B)d\underline{x}_A d\underline{x}_B}{\int\cdots\int f(\underline{x}_A, \underline{x}_B | \underline{m}_A, \underline{m}_B)d\underline{x}_A d\underline{x}_B}$$

$$= \frac{\int\cdots\int \begin{bmatrix}x_{A1}\\x_{B1}\end{bmatrix} f(\gamma_{Ak}, \underline{x}_A, \gamma_{Bl}, \underline{x}_B | \underline{m}_A, \underline{m}_B)d\underline{x}_A d\gamma_{Ak} d\underline{x}_B d\gamma_{Bl}}{\int\cdots\int f(\gamma_{Ak}, \underline{x}_A, \gamma_{Bl}, \underline{x}_B | \underline{m}_A, \underline{m}_B)d\underline{x}_A d\gamma_{Ak} d\underline{x}_B d\gamma_{Bl}},$$

where $$f(\gamma_{Ak}, \underline{x}_A, \gamma_{Bl}, \underline{x}_B | \underline{m}_A, \underline{m}_B)$$

-continued $$\frac{f(\gamma_{Ak}, \underline{x}_A, \gamma_{Bl}, \underline{x}_B) \prod_{i=1}^{k} f(m_{Ai} | x_{Ai}, \lambda_{Ai}) \prod_{j=1}^{l} f(m_{Bj} | x_{Bj}, \lambda_{Bj})}{f(\underline{m}_A, \underline{m}_B)} \propto$$

$$f(\gamma_{Ak}, \underline{x}_A, \gamma_{Bl}, \underline{x}_B) \prod_{i=1}^{k} f(m_{Ai} | x_{Ai}, \lambda_{Ai}) \prod_{j=1}^{l} f(m_{Bj} | x_{Bj}, \lambda_{Bj}).$$

Note that $$f(\underline{m}_A, \underline{m}_B) = \int \cdots \int f(\gamma_{Ak}, \underline{x}_A, \gamma_{Bl}, \underline{x}_B)$$

$$\prod_{i=1}^{k} f(m_{Ai} | x_{Ai}, \lambda_{Ai}) \times \prod_{j=1}^{l} f(m_{Bj} | x_{Bj}, \lambda_{Bj}) d\underline{x}_A d\gamma_{Ak} d\underline{x}_B d\gamma_{Bl}.$$

All of the above calculations can be done with knowledge of the photon process and detection process PDFs. In the above we have implicitly assumed an ordering of the interactions. In practice, we compute equation (6) for all combinations of the permutations of the signals $\underline{m}_A$ and $\underline{m}_B$. For example, in FIG. 4B there are six possible permutations: ([83A,83B], [83A,83B'], [83A,83"], [83A',83B], [83A', 83B'], 83A',83B"]). We then take the estimate that arose from the ordering that maximized $f(\underline{m}_A, \underline{m}_B)$ as in equation (5).

Computing the integral (6) involves integrating the photon interaction positions over the spatial region that a particular crystal pair occupies. To speed up the computation of this integral we restrict the integration over the regions with the largest probabilities.

With the detector geometry used here, changes in the depth of interaction of $x_{B1}$ have little effect on changes of $x_{A0}$ and $r_{A0}$. Similarly, changes in the depth of interaction of $x_{A1}$ have little effect on changes of $x_{B0}$ and $r_{B0}$. Thus, to reduce the computational complexity of the algorithm, the entrance position $x_{A0}$ and trajectory $r_{A0}$ may be computed from $x_{A1}$ and the maximum likelihood estimation of $x_{B1}$ and similarly $x_{B0}$ and $r_{B0}$ may be calculated from $x_{B1}$ and the maximum likelihood estimation of $x_{A1}$. This will enable us to split the photon process PDF into terms for the photon interactions in each detector module, i.e., $$f(\gamma_{Ak},\underline{x}_A,\gamma_{Bl},\underline{x}_B) \approx f(\gamma_{Ak},\underline{x}_A) f(\gamma_{Bl},\underline{x}_B),$$

where $f(\gamma_{Ak},\underline{x}_A)$ is the product of equations (1) and (2) and $f(\gamma_{Bl},\underline{x}_B)$ is the product of equations (3) and (4). This approximation enables us to decouple the integral (6) into a product of an integral over $x_{A1}, \ldots, x_{Ak},\gamma_{Ak}$ and an integral over $x_{B1}, \ldots, x_{Bk},\gamma_{Bl}$.

Results

The method described above was simulated for different detector modules 100A, 100B having four different parameterized light response schemes shown in Table 1, and with reference to Equation (0), above.

TABLE 1

Parameters of the four light response schemes modeled.

| | $r_p$ | $b_p$ | $r_s$ | $b_s$ | d |
|---|---|---|---|---|---|
| Scheme I | 0.35/H | 0.55 | −0.4/H | 0.45 | $\frac{0.10}{2\sqrt{2\ln 2}}$ |
| Scheme II | 0.1/H | 0.55 | −0.2/H | 0.45 | $\frac{0.10}{2\sqrt{2\ln 2}}$ |
| Scheme III | 0.35/H | 0.55 | −0.4/H | 0.45 | $\frac{0.15}{2\sqrt{2\ln 2}}$ |
| Scheme IV | 0.1/H | 0.55 | −0.2/H | 0.45 | $\frac{0.15}{2\sqrt{2\ln 2}}$ |

The results of the Bayesian LOR estimator with the data from schemes I, II, III, and IV are denoted Bayes I, Bayes II, Bayes III, and Bayes IV, respectively. Since the LOR estimations using convention Anger logic did not vary with the data from the different schemes, we only show the results of Anger estimation with scheme I.

Statistics of the performance of the various estimators to correctly position the first point of interaction are shown in Table 2. The misorder rates displayed in Table 2 may seem high, but if one were to randomly guess which interaction was first, then the misorder rate would be approximately:

$$P(\hat{i}_1 \neq i_1 | N \geq 2) = \frac{1}{P(N \geq 2)} \sum_{n=2}^{\infty} P(\hat{i}_1 \neq i_1 | N = n) P(N = n) \approx 57.79\%.$$

In the above we used the data from FIG. 6 to estimate $P(N=n)$ and $$P(\hat{i}_1 \neq i_1 | N = n) = \frac{n-1}{n}.$$

TABLE 2

Statistics of the estimation performance of various LOR estimation algorithms.

| | Depth Bias | Depth Variance | Misorder Rate | Mean Position Error |
|---|---|---|---|---|
| Anger | −0.15 mm | 28.00 mm² | — | 5.40 mm |
| Bayes I | 0.16 mm | 2.42 mm² | 23.54% | 1.62 mm |
| Bayes II | 0.16 mm | 3.94 mm² | 24.22% | 2.01 mm |
| Bayes III | 0.15 mm | 2.66 mm² | 23.53% | 1.70 mm |
| Bayes IV | 0.11 mm | 5.29 mm² | 24.82% | 2.28 mm |
| Ideal | 0 mm | 0 mm² | 0% | 0.77 mm |

The depth bias and variance are the sample mean and variance of the difference of the true and estimated depth of the first interaction. The mean position error is the sample mean of the (3D) Euclidean norm of the difference between the true and estimated interaction positions.

Our model assumes that each signal pair was produced by exactly one high-energy photon interaction. Approximately 26% of the interaction sequences of the high-energy photons violate this assumption. Signals from two separate interactions within the same light-sharing crystal pair are summed together in our simulation. We will refer to the interaction where there are multiple interactions in one dMiCE crystal pair as pair-multiples.

We filter out the coincidences with pair-multiples to quantify their effect on the accuracy of our algorithm. We also compute estimates of the coincidence data where we assume that the correct order of the signals is known. The results of filtering out the coincidences with pair-multiples and the estimates where the signal order is assumed known are shown in Table 4. In practice, one cannot filter out the pair-multiple interactions or know the correct order of the signal pairs. We display these results only to help quantify the source of errors in our Bayesian LOR estimation algorithm.

TABLE 3

Statistics of the estimation performance of the Bayesian LOR estimation algorithm on modified data.

|  | Depth Bias | Depth Variance | Misorder Rate | Mean Position Error |
|---|---|---|---|---|
| Bayes I, no pair-multiples | 0.02 mm | 0.77 mm$^2$ | 19.62% | 1.36 mm |
| Bayes I, correct order | 0.13 mm | 2.49 mm$^2$ | 0% | 1.29 mm |
| Bayes I, no pair-multiples and correct order | 0.02 mm | 0.87 mm$^2$ | 0% | 1.08 mm |
| Bayes IV, no pair-multiples | −0.06 mm | 4.12 mm$^2$ | 22.08% | 2.15 mm |
| Bayes IV, correct order | 0.04 mm | 5.40 mm$^2$ | 0% | 1.97 mm |
| Bayes IV, no pair-multiples and correct order | −0.08 mm | 4.14 mm$^2$ | 0% | 1.85 mm |

The data labeled no pair-multiples shows the results of the coincidences without pair-multiple interactions. The data labeled correct order assumes that the order of the signals is known.

DISCUSSION AND CONCLUSION

We have developed a statistical LOR estimator for PET systems. For exemplary purposes, results are shown using dMiCE crystal pair detector elements. The algorithm estimates an LOR by choosing the most likely order of interactions and then the positions of the first points of interaction for a pair of annihilation photons are calculated by Bayesian estimation. By estimating both photons of an annihilation pair simultaneously, we have reduced the number of unknowns such as the trajectory and entrance position of the photons as they enter the detector modules. Initial numerical experiments illustrate the robustness of our Bayesian LOR estimation algorithm.

Our Bayesian LOR estimation algorithm was also tested with a more sophisticated PDF of the photon process that included a term that estimated the probability of photon escape in the case where the last interaction was a scattering interaction. The direction traveled by the photon after the last scattering interaction is limited to a cone whose aperture is determined by the final energy deposition in the detector. Thus, the probability of escape must be calculated by marginalizing over all the directions contained in this scattering cone. This turned out to be a significant computational burden on the estimation algorithm, while providing no significant improvement in accuracy, and thus, was not considered in the numerical experiments described in this paper.

The model for the distributions of the light response function (the detection process) described in the results section was used in this paper to demonstrate the performance of our Bayesian LOR estimator, but it should be noted that any light response function that varies with depth of interaction could be employed. The model used in our numerical experiments is based on results of some initial testing on the distribution of the light response.

Also, it will be appreciated by persons of skill in the art that other statistical estimation methods, such as a maximum likelihood method may alternatively be used, a Bayesian estimation is believed to be the preferable estimation technique for an $L^2$ cost function. A more appropriate cost function for a task such as LOR estimation would be $L^1$, which would lead to an estimation based on a conditional median rather than a conditional expectation, which is used with Bayesian estimation. Since the distributions used in our models were nearly symmetric and decayed exponentially, the difference between these two estimation methods is expected to be negligible. An $L^1$ cost function also leads to a more computationally intensive algorithm.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for estimating the line of response for a coincident detection in a positron emission tomography scanner comprising the steps:
    (a) identifying a coincident event in a positron emission tomography scanner wherein a first detector module detects at least one photon-producing interaction and a second detector module disposed opposite the first detector module detects a plurality of photon-producing interactions, and wherein all of said photon-producing interactions in both the first and second detector modules occur close enough in time to be coincident for purposes of positron emission tomography;
    (b) selecting one of the at least one photon-producing interactions in the first detector module, and selecting one of the plurality of photon-producing interactions in the second detector module;
    (c) calculating the joint probability that the selected photon-producing interaction in the first detector module and the selected photon-producing interactions in the second detector module are the first occurring photon-producing interactions in both detector modules for the identified coincident event;
    (d) repeating steps (b) and (c) for all permutations of photon-producing interactions in the first detector module and photon-producing interactions in the second detector module;
    (e) using the permutation having the largest calculated joint probability to construct an estimated line of response.

2. The method of claim 1, wherein the step of calculating the joint probability comprises calculating a joint probability density function that includes factors accounting for Compton scattering interactions in each of the first and second detector modules and factors accounting for a final interaction in each of the first and second detector modules.

3. The method of claim 2, wherein the factors accounting for the final interactions in the first and second detector modules include terms that account for Compton scattering and photoelectric absorption.

4. The method of claim 1, wherein the first and second detector modules comprise detector elements adapted to produce signals that depend on the depth of interaction within the detector element.

5. The method of claim 4, wherein the detector elements comprise crystal pairs having a reflector element therebetween, wherein each crystal of the crystal pair further comprises an associated photodetector.

6. The method of claim 2, wherein a Bayesian estimation is used for calculating the joint probability that the selected photon-producing interactions are the first occurring photon-producing interactions in both of the first and second detector modules for the identified coincident event.

7. The method of claim 6, wherein the Bayesian estimation also calculates an estimated position of the selected photon-producing interactions in the first and second detector modules.

8. The method of claim 1, further comprising the step of discarding the identified event if the largest calculated joint probability is less than a selected threshold.

9. The method of claim 8, wherein the selected threshold is determined experimentally.

10. A method for estimating the line of response in a positron emission tomography scanner comprising the steps:
 (a) identifying a coincident event in a scanner having a plurality of detector modules arranged in a ring by identifying photodetector signals from a first detector module and photodetector signals from a second detector module within a field of view of the first detector module that occur within a predetermined span of time, and wherein the first detector module detects one or more first interactions and the second detector module detects one or more second interactions;
 (b) for each combination of interactions comprising one of the first interactions and one of the second interactions: calculating the joint probability that the combination of interactions are the first occurring interactions in both detector modules for the identified coincident event;
 (c) using the combination of interactions having the largest calculated joint probability to construct an estimated line of response.

11. The method of claim 10, wherein the step of calculating the joint probability comprises calculating a joint probability density function that includes factors accounting for Compton scattering interactions in each of the first and second detector modules.

12. The method of claim 11, wherein the joint probability density function further comprises factors accounting for a final interaction in each of the first and second detector modules, wherein the factors accounting for the final interactions in the first and second detector modules include terms that account for Compton scattering and photoelectric absorption.

13. The method of claim 10, wherein the first and second detector modules comprise detector elements adapted to produce signals that depend on the depth of interaction within the detector element.

14. The method of claim 13, wherein the detector elements comprise crystal pairs having a reflector element therebetween, wherein each crystal of the crystal pair further comprises an associated photodetector.

15. The method of claim 11, wherein a Bayesian estimation is used for calculating the joint probability that the combination of interactions are the first occurring interactions in both of the first and second detector modules for the identified coincident event.

16. The method of claim 15, wherein the Bayesian estimation also calculates an estimated position of each of the interactions in the combination of interactions in the first and second detector modules.

17. The method of claim 10, further comprising the step of discarding the identified event if the largest calculated joint probability is less than a selected threshold.

18. The method of claim 17, wherein the selected threshold is determined experimentally.

* * * * *